(12) United States Patent
Rovatti

(10) Patent No.: US 8,388,567 B2
(45) Date of Patent: Mar. 5, 2013

(54) APPARATUS FOR EXTRACORPOREAL BLOOD TREATMENT

(75) Inventor: Paolo Rovatti, Finale Emilia (IT)

(73) Assignee: Gambro Lundia AB, Lund (SE)

( * ) Notice: Subject to any disclaimer, the term of this patent is extended or adjusted under 35 U.S.C. 154(b) by 728 days.

(21) Appl. No.: 12/595,164

(22) PCT Filed: Apr. 12, 2007

(86) PCT No.: PCT/IB2007/000946
§ 371 (c)(1),
(2), (4) Date: Dec. 21, 2009

(87) PCT Pub. No.: WO2008/125894
PCT Pub. Date: Oct. 23, 2008

(65) Prior Publication Data
US 2010/0114005 A1 May 6, 2010

(51) Int. Cl.
*A61M 37/00* (2006.01)
(52) U.S. Cl. .................. 604/6.15; 604/6.11
(58) Field of Classification Search ........ 604/4.01–6.16; 422/44–48; 436/16; 73/1.01, 1.16, 149
See application file for complete search history.

(56) References Cited

U.S. PATENT DOCUMENTS

| | | | |
|---|---|---|---|
| 4,898,576 A | 2/1990 | Philip | |
| 5,213,573 A | 5/1993 | Sorich et al. | |
| 5,738,824 A | 4/1998 | Pfeifer | |
| 7,255,680 B1 | 8/2007 | Gharib | |
| 7,364,563 B2 * | 4/2008 | Lucke et al. | 604/6.15 |
| 7,794,419 B2 * | 9/2010 | Paolini et al. | 604/6.06 |
| 2005/0043665 A1 | 2/2005 | Vinci et al. | |

FOREIGN PATENT DOCUMENTS

| | | |
|---|---|---|
| EP | 0 387 724 A2 | 9/1990 |
| EP | 0 458 910 A1 | 12/1991 |
| EP | 0 784 493 A1 | 7/1997 |
| WO | 91/09229 A1 | 6/1991 |
| WO | 96/08288 A1 | 3/1996 |
| WO | 01/30422 A1 | 5/2001 |
| WO | 03/055542 A1 | 7/2003 |
| WO | 2006/123197 A1 | 11/2006 |
| WO | WO 2006/123197 | * 11/2006 |

* cited by examiner

*Primary Examiner* — Philip R Wiest
(74) *Attorney, Agent, or Firm* — Pearne & Gordon LLP

(57) ABSTRACT

In an apparatus for extracorporeal blood treatment, an extracorporeal circuit (6) is connected to a blood chamber (3) of a membrane device (2). A pump (10) displaces a priming fluid from a source of a priming fluid (9) to a drainage (11) for discharging the priming fluid. A control unit (13) is provided with a processor which controls the pump at a preset first flow rate value, and receives from a pressure sensor (12) a first pressure value, compares the first pressure value with a reference pressure value and, on the basis of this comparison, determines whether or not the extracorporeal circuit is of a pediatric type or of an adult type. The invention is particularly useful during a stage of readying a dialysis apparatus.

32 Claims, 3 Drawing Sheets

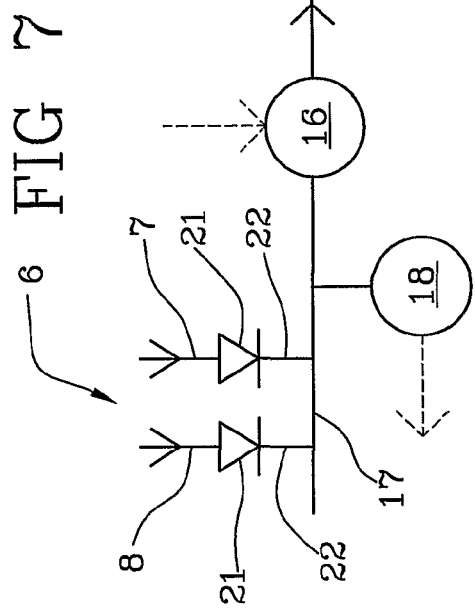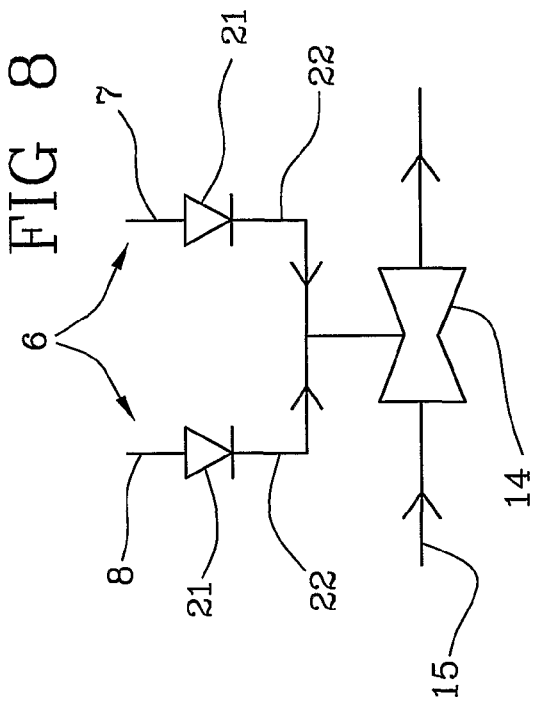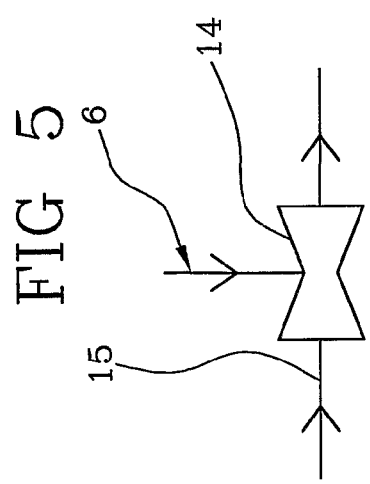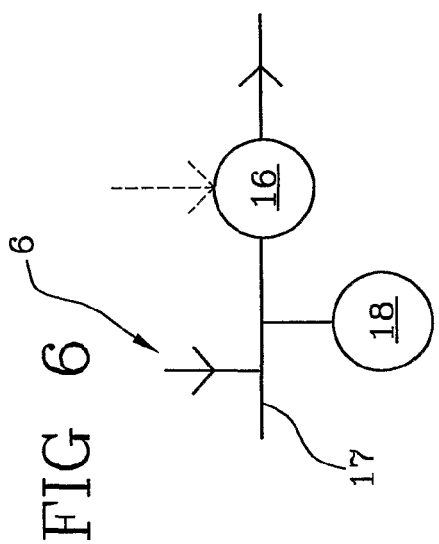

APPARATUS FOR EXTRACORPOREAL BLOOD TREATMENT

BACKGROUND OF THE INVENTION

The invention relates to an apparatus for extracorporeal blood treatment, and a method for readying the apparatus.

Specifically, though not exclusively, the invention can be usefully applied in verification of a correct readying of a medical apparatus using an extracorporeal blood circuit, such as for example a hemodialysis or hemo(dia)filtration apparatus.

An apparatus for extracorporeal blood treatment includes a stage, preliminary to treatment true and proper, in which the disposable extracorporeal blood circuit, is coupled to the treatment control monitor (for example a dialysis monitor). This stage, which is performed before connecting up the extracorporeal blood circuit to the patient, includes connection of the blood transport lines (in general an arterial line for blood removal from the patient, and a venous line for blood return to the patient) to a membrane device for blood treatment (for example a hemodialyser in a case of hemodialysis), which in turn is connected up to a treatment fluid supply circuit (for example a dialysis fluid) and to a used treatment fluid discharge circuit. The membrane device for blood treatment comprises a semi-permeable membrane which divides a blood compartment, connected to the blood transport lines, and a fluid compartment, connected to the above-mentioned supply and discharge circuits. The blood transport lines are further coupled to a sensor and actuator system equipped on the dialysis monitor, which system normally comprises means for blood circulation (for example a blood pump, usually peristaltic), pressure sensors, an air bubble sensor, one or more circuit blocking clamps, etc. Before connection of the extracorporeal blood circuit to the patient's vascular system, a priming stage is usually performed of the blood transport lines and the blood treatment device, which are filled with a priming liquid (usually an isotonic saline solution or another patient-isotonic liquid) which performs the function of expelling air, filling and rinsing.

One of the drawbacks in the prior art derives from the fact that usually the dialysis monitor can be predisposed to receive various types of extracorporeal circuits suitable for effecting different treatments on different patients; in particular the monitor can serve for treatment of adult patients and children. In the two cases, the parameters regulating the treatment, which are preset by the operator, are very different. For example, the blood flow rate is usually lower when a child is to be treated; also the weight loss and the anticoagulant flow rate are lower. Similarly, the extracorporeal blood circuits used are of different types, especially as regards the dimensions of the components of the circuit. For example, the diameter of the blood transport lines is usually smaller in a pediatric extracorporeal circuit.

A grave risk for the health of a patient arises if a circuit suitable for one type of treatment (for example a blood line for an adult) is readied on a dialysis monitor set with parameters suitable for a different type of treatment (for example a treatment for a child). To reduce the risk a security system is predisposed, provided with means for recognising the type of dialysis circuit which is coupled to the monitor. The known means of recognition comprise an optical reading system which reads an identifying signal, for example a bar code, applied to the extracorporeal circuit. The known security systems for recognition of the extracorporeal circuit in an apparatus for extracorporeal blood treatment are liable to improvement in terms of both cost and reliability.

Also known is monitoring the flow resistance in a fluid transport tube, in which an increase in the flow resistance, signalled by an increase in pressure in the tube, provides an indication of the presence of an occlusion in the tube.

U.S. Pat. No. 4,898,576 describes a method which instead of simply waiting for a pressure increase in the fluid transport line, causes a controlled variation in the flow along the line, then measures the pressure variation due to the flow variation, and thus determines the flow resistance offered by the transport line on the basis of the above-mentioned variations.

EP 387724 describes a vascular infusion apparatus provided with an infusion line on which a peristaltic infusion pump and a pressure sensor downstream of the pump operate. A controller is programmed to increase the pump velocity periodically and for a brief time so that at each perturbation of the system a determined volume of liquid is added to the normal equilibrium flow. The pressure is measured and the pressure change with respect to the equilibrium flow, i.e. the change in pressure due to the perturbation, is integrated and divided by the volume of added liquid during the perturbation so as to determine the resistance to the fluid flow. By considering also the duration of the perturbation, the compliance of the infusion line can be determined.

EP 784493 describes two monitoring methods of the flow resistance in an infusion apparatus provided with a peristaltic pump, the first used for high flow and the second for low flow. In the first, high-flow method, the pressure is calculated at two different flow rates and the processor calculates the resistance as being equal to the pressure change divided by the flow rate change. The second method, for low flow-rates, involves pumping an intermittent flow and measuring the corresponding pressure signal. The pressures in the absence of flow are subtracted from those in the presence of flow. Then the pressure differences thus obtained are processed using a mathematical model in order to obtain the tube resistance.

U.S. Pat. No. 5,213,573 describes a method for monitoring the appropriate functioning of an IV administration set, in which an infusion pump is alternatingly commanded in order to remove a predetermined volume of fluid from a patient at a first pressure during a predetermined interval of time, and in order to infuse a predetermined volume of fluid to the patient at a second pressure in a second time interval. An eventual presence of an anomalous flow through the IV administration set is revealed by a comparison between the above-mentioned pressures. The anomalous flow can be caused, for example, by an incorrect positioning of the needle in the vascular access, such as to cause infiltration into the patient's tissue.

EP 458910 describes an apparatus provided with a peristaltic pump and a device for measuring the diameter of a transport tube associated to the pump, and which consequently regulates the pump velocity in accordance with a possible changing of the tube diameter in order to maintain the infusion flow rate at a constant level.

The prior art further comprises various systems for determining the actual blood flow rate generated by a peristaltic pump in an extracorporeal blood transport line, such as for example in WO 03/055542, which uses a memorised predetermined calibration function, the principal values of which are the angular velocity of the pump, the arterial pressure upstream of the pump, the effective blood flow rate and the work time since start of treatment of the tract of line coupled to the pump. Calibration functions can be used that also contain the following variables: the geometric characteristic of the vascular access in which the extracorporeal circuit removes blood from the patient, the length of the tract of arterial line upstream of the peristaltic pump, the pressure downstream of the peristaltic pump, the temperature of the extracorporeal circuit and the value of the blood hematocrit of the patient. From the values measured during the course of the treatment of the above variables, by use of the calibration function a precise value for the effective flow rate of the blood flow can be calculated.

SUMMARY OF THE INVENTION

An aim of the present invention is to provide an apparatus for extracorporeal blood treatment which is provided with a system able to recognise the type of extracorporeal circuit applied to the apparatus itself.

A further aim of the invention is to realise a method for readying the extracorporeal blood treatment apparatus with which the type of extracorporeal circuit applied on the apparatus can be recognised.

An advantage of the invention is to provide an apparatus which is constructionally simple and economical.

A further advantage is to make available an apparatus and a method by means of which an extracorporeal circuit suitable for an adult patient can be clearly distinguished from a pediatric extracorporeal circuit type.

A still further advantage is to give rise to an apparatus and a method which are able to reduce the risk of performing an extracorporeal blood treatment not suitable for the extracorporeal circuit mounted on the apparatus.

The recognition system of the extracorporeal circuit realised in agreement with the present invention can serve as a further security system (protection system) contemporaneously with a further security system based, for example, on the use of an optical sensor.

These aims and others besides are all attained by the invention as it is claimed in one or more of the appended claims.

In a specific preferred embodiment of the invention, a line of the extracorporeal circuit will be connected to a discharge (or drainage) whose resistance to flow is known; the flow resistance offered by the above-mentioned line will be determined, as the pressure in at least one point of the line and the flow rate along the line itself are known; by means of the above, a conclusion will be reached as to whether the line has a passage section which is relatively large (for adults) or relatively small (for a pediatric line).

Further characteristics and advantages of the present invention will better emerge from the detailed description that follows, of at least a preferred embodiment of the invention, illustrated purely by way of non-limiting example in the accompanying figures of the drawings.

BRIEF DESCRIPTION OF THE DRAWINGS

The description will be made with reference to the accompanying figures of the drawings, provided by way of non-limiting example, in which.

FIGS. from 5 to 8 illustrate four embodiments of drainage systems that can be used with the embodiments of FIGS. from 1 to 4.

DETAILED DESCRIPTION

Figure 1:
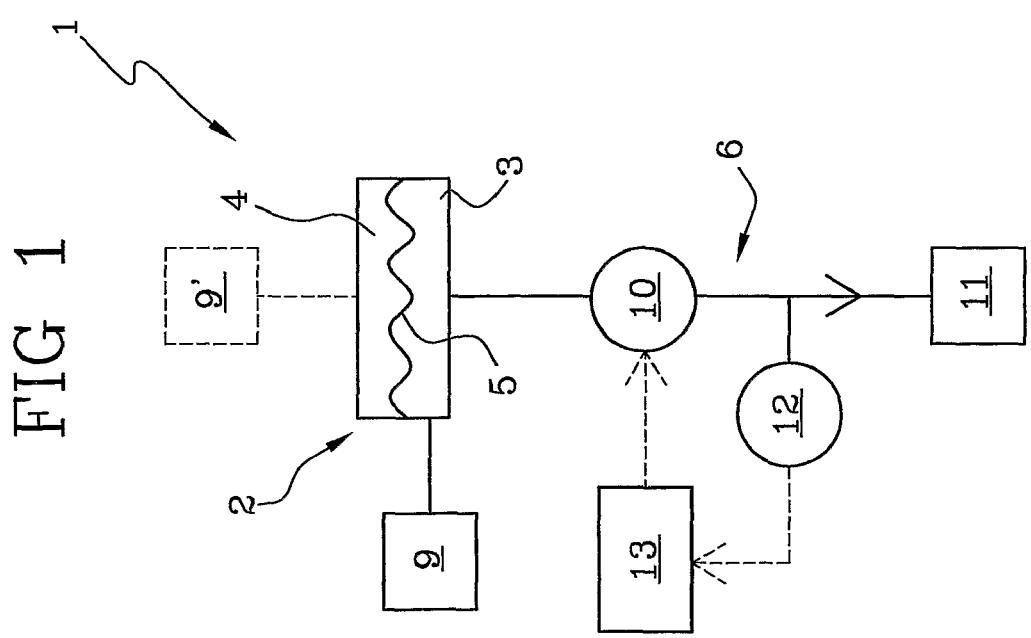
FIG. 1 illustrates a first embodiment of an apparatus for extracorporeal blood treatment in agreement with the present invention.

With reference to FIG. 1, 1 denotes in its entirety an apparatus for extracorporeal blood treatment. The apparatus 1 can be constituted by a hemodialysis apparatus and/or a hemo (dia)filtration apparatus.

The apparatus 1 comprises a membrane device 2 for extracorporeal blood treatment. The membrane device 2 in turn comprises a blood chamber 3 and a fluid chamber 4 separated from one another by a semipermeable membrane 5. The membrane device 2 can be constituted by any type of hemodialyser or hemo(dia)filter of known type.

The apparatus 1 comprises an extracorporeal circuit 6 connected to the blood chamber 3 of the membrane device 2. The extracorporeal circuit 6 can be constituted by any extracorporeal circuit or hemodialysis or hemo(dia)filtration set of known type. In the present embodiment the extracorporeal circuit 6 is represented schematically as a single line connected to the blood chamber 3. The extracorporeal circuit can comprise an arterial line and a venous line, denoted respectively by 7 and 8 in FIGS. from 2 to 4, each of which is provided with one or more of the following components (of known type and not illustrated): one or more separation chambers of air/blood and/or mixing chambers of blood with another liquid introduced into the circuit; a pump segment (normally present only on the arterial line 7 in a case of double-needle treatment); access sites for injection or removal; auxiliary lines for introduction of special fluids, such as the priming fluid line, the anticoagulant line (normally only on the arterial line 7), the replacement fluid line (in pre- and/or post-dilution), the infusion fluid line; at least an auxialiary line for detecting a pressure signal; connectors for the various elements to which the circuit is connected, including in particular the membrane device 2, the vascular access device and the above-mentioned special fluid sources; manual line-closing clamps; and so on. The extracorporeal circuit is represented in FIG. 1 (as in FIGS. from 2 to 4) in the priming configuration. Priming is a procedure carried out preliminarily to connection of the extracorporeal circuit 6 to the patient and to the treatment true and proper, in which the circuit is emptied of air and filled and rinsed with a priming fluid, usually a fluid that is isotonic to the patient. In FIGS. from 2 to 4 some other possible priming configurations are shown, in which the present invention can be applied.

In the priming configuration, the apparatus 1 comprises a priming fluid source 9 connected to the extracorporeal circuit 6. The priming fluid can be, for example, a saline isotonic solution, or a dialysis solution, or a further solution which is isotonic to the patient, or even other watery solutions. The source 9 comprises, in the specific case, a container (for example a flexible-walled bag) connected to the venous line 8 by means of an auxiliary line. In FIG. 1, a broken line is used to denote a first further source 9' usable (alternatively or additionally to the source 9, i.e. to the container on the venous line). The first further source 9' is connected to the fluid chamber 4 of the membrane device 2 to provide a priming fluid to the extracorporeal circuit 6 by retrofiltration (backfiltration) through the semipermeable membrane 5. The first source 9' can comprise the fluid circuit (of known type and not illustrated) which, in an apparatus for extracorporeal blood treatment (for example a hemodialysis and/or hemo(dia)filtration apparatus), is connected to the fluid chamber of the membrane device 4. The fluid circuit is able to supply (in a known way which is not described herein) a treatment fluid (for example a dialysis fluid) at predefined temperature and concentration conditions, in predefined ways (of known type and not described herein) for controlling the flow rate and/or the pressure. The fluid circuit is further able to discharge the waste fluid in a drainage. The fluid circuit can be constituted by any known circuit for preparation and discharge of a dialysis liquid in a hemodialysis and/or hemo(dia)filtration apparatus of known type. The fluid circuit comprises, in the example, at least the following elements, of known type: a device for on-line preparation of a dialysis fluid from water and concentrates; one or more fluid-degassing units; a fluid heating device; one or more fluid ultrafiltration units for reduction of bacteria and endotoxins; a fluid balancing device for controlling the patient weight-loss; a heat and/or chemical disinfection circuit; sensors for monitoring the various parameters, such as the fluid pH, the presence of blood loss coming from the membrane device 2, the dialysance of the membrane device 2, the hematocrit of the blood in the extracorporeal circuit, the presence of air bubbles in the blood circulating along the extracorporeal circuit, etc.

The apparatus 1 comprises a pump 10 connected to the extracorporeal circuit 6 for the displacement of fluid. In the specific case of FIG. 1, the pump 10 is constituted by any blood pump of known type arranged along the extracorporeal circuit 6. In particular the pump 10 can be arranged on the arterial line 7 as is illustrated in the examples from FIGS. 2 to 4. The pump 10 is constituted by a positive-displacement pump. In particular the pump 10 is constituted by a tube deformation pump (peristaltic), for example a rotary peristaltic pump.

The apparatus 1 comprises a drainage 11 connected to at least an end of the extracorporeal circuit 6, for discharge of the priming fluid. In the special case the drainage 11 is connected to an end of the extracorporeal circuit 6. In the illustrated embodiment the end be comprise either one or the other of the patient ends of the arterial or venous lines. In general, in an extracorporeal circuit the patent ends are the ends configured for the connection with the vascular access device for access to the patient's vascular system. The patient ends of each arterial line and venous line are opposite the corresponding device ends which are the ends configured for the connection with the blood chamber of the membrane device.

The apparatus 1 comprises a pressure sensor 12 connected to the extracorporeal circuit 6. The pressure sensor 12 can comprise any one of the sensors used in the prior art for the detection of the pressure in an extracorporeal blood circuit. The pressure sensor 12, in the case of FIG. 1, operates in a tract of the extracorporeal circuit arranged between the pump 10 and the priming fluid dishcarge end. The pressure sensor 12 operates between the pump 10 and the drainage 11. The pressure sensor 12 can be, for example, of the deformable membrane type, in which a membrane exhibits a side in contact with the inside of a chamber arranged along the extracorporeal circuit and the opposite side communicating with a pressure transducer connected in turn to a control unit 13 of the apparatus. The control unit 13 receives the signal for the monitoring of the circuit 6 pressure. The pressure sensor 12 can alternatively comprise a tube which places the extracorporeal circuit (in general an blood/air separation chamber) in communication with the pressure transducer and which is provided with a transducer-protector device having a hydrophobic membrane (also known as a blood catcher) of known type.

The apparatus 1 comprises a memory (which can be inserted in the control unit 13) containing at least one reference value $V_R$ for discriminating a first type of extracorporeal circuit from a second type of extracorporeal circuit. Two or more reference values can be memorised $V_{R1}$, $V_{R2}$, etc., which discriminate between three or more different types of extracorporeal circuit. In the specific case, the first type of extracorporeal circuit is different to the second type of extracorporeal circuit in the nominal fluid passage section in at least one tract of the circuit. In greater detail, the two types of extracorporeal circuit which can be associated to the apparatus 1 disposably (generally single-use or a limited number of uses) comprise a first type of circuit suitable for performing treatments on adult patients (blood line for adults), and a second type of circuit suitable for performing treatment on child patients (pediatric blood line). The two types of circuits, for adults and children, differ among other things in the internal diameter of the blood trasnport tube; this diameter is greater in extracorporeal circuits for adults and smaller in extracorporeal circuits for children. As is known, in the setting-up of an extracorporeal treatment for a child in general, the set or desired values of the flow rates of the various fluids to be used in the treatment (blood flow rate, anticoagulant flow rate, dialysis fluid flow rate, replacement fluid flow rate, infusion fluid flow rate etc.) are lower than the corresponding set or desired values for a treatment destined for an adult.

The apparatus 1 further comprises a user interface for enabling dialogue between the operator and the control unit 13 (for example for setting apparatus treatment parameters, for entering or requesting data in or from the control unit 13, for changing the treatment parameters, for receiving instructions or alarms from the control unit, etc.). The user interface (known and not illustrated) can comprise any user interface used in the prior art for an extracorporeal blood treatment, such as for example an interface of a machine for hemodialysis or hemo(dia)filtration.

The apparatus 1 comprises a processor (which can be inserted in the control unit 13) which is connected to the pump 10, to the pressure sensor 12 and to the memory. The processor is programmed to perform the following operations:

a) controlling the pump 10 to move the priming fluid along the extracorporeal circuit 6 to a first set or desired flow rate value $Q_1$;

b) receiving from the pressure sensor 12 a first pressure value $P_1$ at the first first flow rate value $Q_1$ (it is known that the actual flow rate may be different than the set or desired flow rate; a system for measuring or determining the actual flow rate—for example a calculation system of a known type—can be implemented on the apparatus);

c) receiving the reference value $V_R$ from the memory;

d) processing the first flow rate value $Q_1$ (and/or the actual—calculated or measured—flow rate value) and/or the first pressure value $P_1$ with the first reference value $V_R$;

e) determining, on the basis of the result of the above processing, if the extracorporeal circuit belongs (or not) to the first type or the second type of extracorporeal circuit.

In the described embodiment the above operation d), the processing, comprises the sub-operation of calculating a parameter which is indicative of the flow resistance of a tract of extracorporeal circuit in nominal conditions, in which the calculation uses a mathematical model which relates the pressure, the flow rate (set or desired or actual) and the flow rate resistance of the tract of circuit. In greater detail, the mathematical model can be represented by the formula $R=\Delta P/Q$, where R is the flow resistance of the tract of circuit, $\Delta P$ is the fall in pressure between two points of the tract of circuit which are distant from one another, and in which the pressure results or is at least determinable, Q is the flow rate (set or desired or actual) crossing the tract of circuit. The tract of circuit which is considered in the calculation is a tract of blood transport tube having a constant-diameter transversal section and going from the pressure sensor 10 to the drainage 11. The pressure $P_D$ at the drainage 11 has a substantially known value. By measuring the pressure $P_1$ at the point where the sensor 10 operates, and knowing the flow rate $Q_1$ along the extracorporeal circuit on the basis, for example, of the velocity $\Omega_1$ of the positive-displacement pump 10 (or determining the actual flow rate by means of any one of the known calculation methods or by a flow detection), it is possible to calculate the resistance $R_1$ of the tract of circuit $R_1=(P_1-P_D)/Q_1$. The reference value $V_F$ can comprise, for example, a flow resistance value $R_F$ able to discriminate between a circuit for adults and a circuit for children. In this case stage e) of determining the type of circuit will comprise the comparison between $R_1$ and $R_F$: if $R_1<R_F$, then the circuit coupled to the apparatus is a circuit for adults, while if $R_1>R_F$, the circuit is a pediatric one. In another case the reference value $V_F$ can comprise, for example, a predetermined pressure value $P_F$. In this case drainage pressure $P_D$ is known during the priming stage, so the value of the pressure $P_1$ is detected at a predetermined priming flow rate $Q_P$ (set or actual value), and thus the value $P_1$ is compared with the reference value $P_F$: if $P_1<P_F$, the circuit is an adult one, while if $P_1>P_F$ the circuit is a pediatric one. In this case too the mathematical model linking pressure, flow rate and flow rate resistance is used, in the following correlation: $R_F=(P_F-P_D)/Q_P$, where $R_F$ is the resistance of a (hypothetical or real) reference circuit, $P_F$ is the pressure measured by the pressure sensor 12 applied to the reference circuit by predetermined priming flow rate $Q_P$ (set or actual), $P_D$ is the pressure (known) at the drainage at the predetermined flow rate $Q_P$, so that in substance the above-used reference value $P_F$ is equal to $R_F*Q_P+P_D$. In a third case the reference value $V_F$ can comprise, for example, a predetermined flow rate value $Q_F$. In this third case a priming condition is preset in order to obtain a set value $P_P$ of the priming pressure from the sensor 12, after which the corresponding value of the flow rate $Q_1$ is detected (for example on the basis of the pump velocity 10 measured by a sensor which known and not illustrated), which flow rate value $Q_1$ is compared with the reference value $Q_F$. If $Q_1>Q_F$, the circuit is of the adult type, while if $Q_1<Q_F$ the circuit is a pediatric one. In this case too the drainage pressure $P_D$ is considered to be known and the correlation between pressure, flow rate and flow rate resistance is implicitly used with the following formula $R_F=(P_P-P_D)/Q_F$, where $R_F$ is the resistance of a (hypothetical or real) reference circuit, $Q_F$ is the circulating flow rate in a reference circuit, produced by the pump 10 at the predetermined priming pressure $P_P$ (set), $P_D$ is the pressure (known) at the drainage, so that the above reference value $Q_F$ is substantially equal to $(P_P-P_D)/R_F$.

Stage d) of the processing can also include the use of other mathematical models, such as for example those described in EP 784493, which is incorporated herein for reference in those parts where it describes how to determine the resistance of a fluid circuit. The use of the mathematical model described by the formula $R=(P_2-P_1)/(Q_2-Q_1)$ comprises the operations of measuring two pressure values $P_1$ and $P_2$ at two different flow rates $Q_1$ and $Q_2$ in order to calculate the resistance R of a tract of fluid transport tube to be compared with at least one reference value, for example a reference resistance which discriminates between a blood line tube for adults and a pediatric blood line tube. With regard to the use of more complex mathematical models for the determination of the circuit flow rate resistance, see the description of EP 784493.

Figure 4:
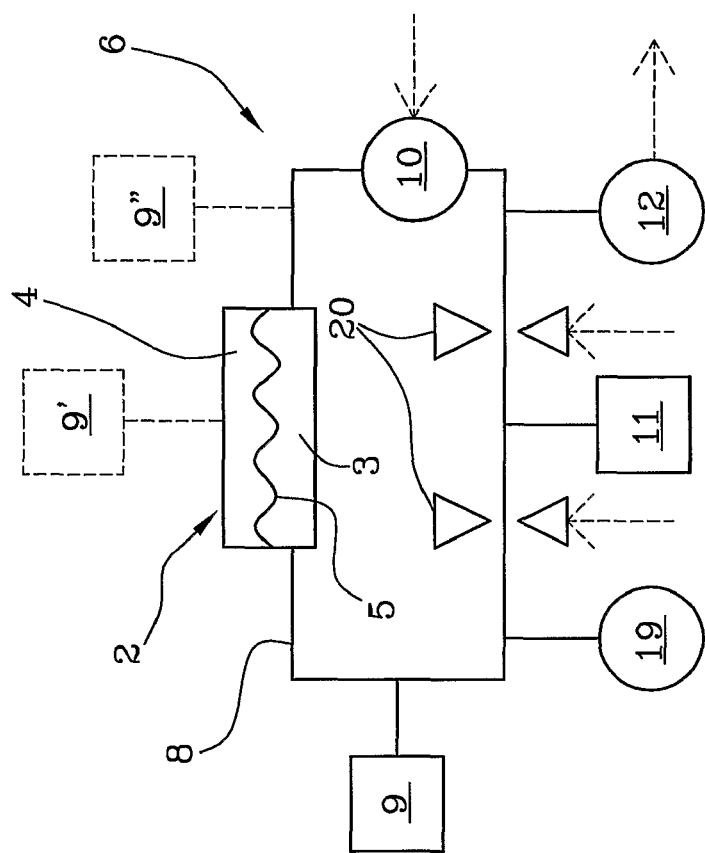
FIG. 4 illustrates a fourth embodiment of an apparatus for extracorporeal blood treatment in agreement with the present invention.

The extracorporeal circuit 6 in FIG. 1 is configured so that during operation a) in which the pump 10 is controlled to displace the priming fluid along the extracorporeal circuit 6, and during operation b) of acquiring the pressure from the sensor 12, the priming fluid is moved towards the drainage 11. The same is true for the circuits of the apparatus of FIGS. 2 and 3. FIG. 4, on the other hand, shows an apparatus in which in operations a) and b) of pump control and pressure acquisition, preliminary to the following operation d) of processing the flow rate and/or pressure values, the circuit is ring-configured and the priming fluid is recycled along the ring (in this case the use of two pressure sensors, distanced from one another, is envisaged, with one sensor for example on the arterial line 7 and the other on the venous line 8, in order to place in relation the flow resistance, the pressure drop and the flow rate).

The apparatus 1 comprises means for maintaining a constant or in any case a known pressure in the drainage 11 while the priming fluid is displaced towards the drainage 11. In FIGS. from 5 to 8 four different types of drainage 11 are illustrated. Each of the drainages of FIGS. 5 and 6 (single-connection drainage) is usable as a drainage 11 in each of the apparatus of FIGS. 1, 3 and 4. Each of the drainages of FIGS. 7 and 8 (double-connection drainages) can be used as a drainage 11 in the apparatus of FIG. 2.

With reference to FIG. 5, the drainage 11 is provided with an aspiration device which in the specific case comprises a venturi tube 14 inserted in a fluid line 15. The venturi tube 14 is configured for aspirating fluid from the end of the extracorporeal circuit 6 connected to the drainage 11. The fluid line 15 can comprise a tract of the above-mentioned fluid circuit of the apparatus 1 (dialysis circuit fluid) connected to the fluid chamber 4 of the membrane device 2. The aspiration pressure of the venturi tube 14 is known, for example by the use of sensors (of known type and not illustrated) which are connected to the control unit 13. The aspiration of the venturi tube is adjustable to vary the flow rate along the fluid line 15, using known means and in a known way.

With reference to FIG. 6, the drainage 11 is provided, in this case too, with an aspiration device which in the specific case comprises an aspiration pump 16, for example a positive-displacement pump. The inlet of the aspiration pump 16 is connected to the end of the extracorporeal blood circuit 6 connected to the drainage 11. The aspiration pump 16 is arranged on a fluid line 17 which can, for example, be part of the fluid circuit of the apparatus (dialysis fluid circuit) which is connected to the fluid chamber 4 of the membrane device 2. In particular the fluid line 17 is interposed between an outlet of the fluid chamber 4 and a used treatment fluid discharge (known and not illustrated) which exits the chamber 4 during the course of the treatment. In particular the outlet of the aspiration pump 16 is connected to the above-mentioned used treatment fluid discharge, while the inlet of the aspiration pump 16 is connected to an outlet of the fluid balancing device of the apparatus 1. The fluid line can comprise a tract of the used treatment fluid line. The inlet of the aspiration pump 16 is further connected to a pressure sensor 18 which is in turn connected to the control unit 13 to provide a signal indicating the drainage pressure 11.

The processor of the control unit 13 is programmed to perform the further operations of:
f) acquiring a pressure value $P_D$ at the drainage 11; and
g) also using the pressure value at the drainage $P_D$ in operation d) to be processed.

Some examples of how the above operations f) and g) are performed have been described herein above.

Note that the reference value can comprise, apart from one or more values serving to discriminate between two or more types of circuit, also, in addition or alternatively, two or more ranges of values, each range being associated to a corresponding type of extracorporeal circuit. The value range can comprise flow resistance values, pressure values, flow rate values, or other values which depend on these or which influence them. In this case operations d) and e) of elaborating the pressure/flow rate signal(s) and of determining if the extracorporeal circuit belongs or not to a specific type of extracorporeal circuit, can comprise the sub-operation of verifying which range(s) of reference values the value(s) relating to the pressure/flow rate signal(s) refer(s) to.

The control unit 13 processor is programmed to provide, on the basis of the determination of the type of circuit to which the extracorporeal circuit 6 belongs, a setting for performing a standard treatment suitable for the type of circuit identified. Thus, for example, if the processor determines that the extracorporeal circuit coupled to the extracorporeal treatment apparatus 1 is a pediatric circuit, the processor automatically imposes the parameter for a standard treatment for a child (with the option of confirming or modifying the treatment set via the user interface).

The processor is also programmed to operate in a further modality (the desired modality can be preliminarily selected via the user interface) in which the following operations are performed:

h) acquiring the setting for a treatment to be carried out with the extracorporeal circuit 6;
i) verifying whether the type of circuit to which the extracorporeal circuit belongs is compatible with the treatment to be carried out.

Acquisition of the above-described setting can occur as described above, via the user interface.

As already mentioned, the processor is programmed to perform the further operations of:

j) controlling the pump 10 to displace the priming fluid along the extracorporeal circuit to a second flow rate value $Q_2$;
k) receiving a second pressure value $P_2$ from the pressure sensor 12, at the (set or desired or actual, calculated or measured) second flow rate value $Q_2$;
l) processing the first and second flow rate values $Q_1$ and $Q_2$ and/or the first and second pressure values $P_1$ and $P_2$ with a reference value (or with a range of reference values), or with the reference values (or with the ranges of reference values);
m) determining, on the basis of the result of the above processing, whether the extracorporeal circuit belongs to the first type or the second type of extracorporeal circuit (or to still other types of extracorporeal circuit).

Figure 2:
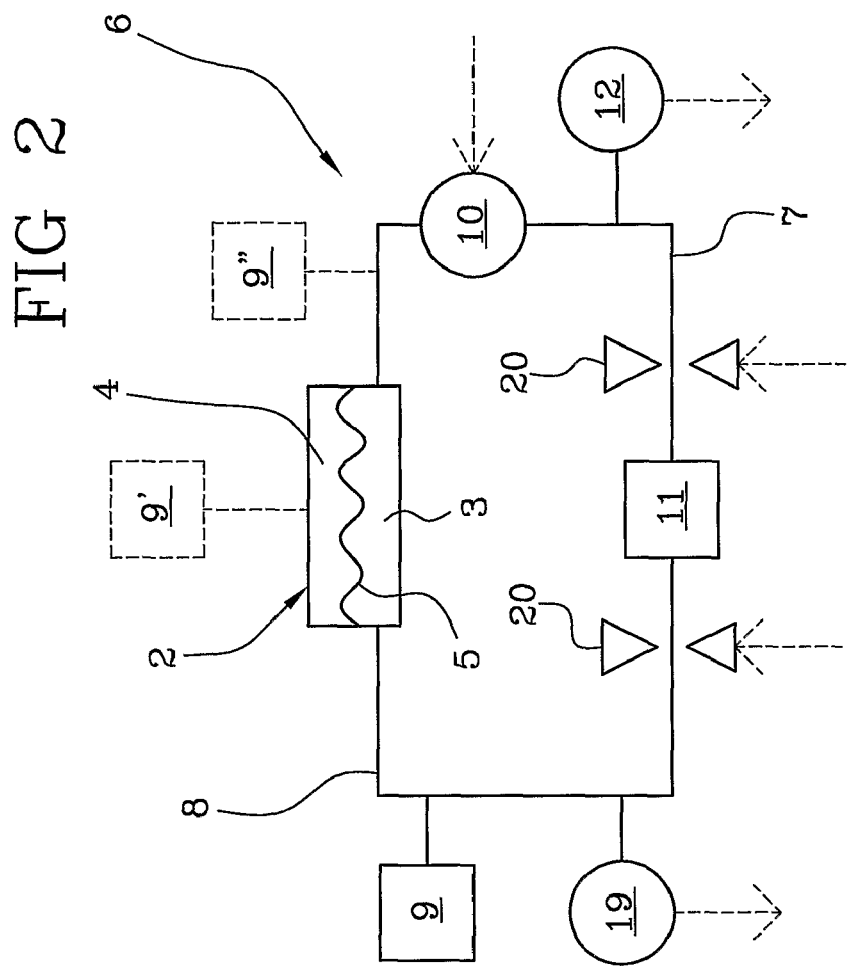
FIG. 2 illustrates a second embodiment of an apparatus for extracorporeal blood treatment in agreement with the present invention.

With reference to FIG. 2, the similar elements to FIG. 1 are denoted using the same numbers. The extracorporeal circuit 6 comprises the arterial line 7 and the venous line 8, each of which exhibits an end connected to the drainage 11. In the specific case the drainage 11 is connected to two ends of the extracorporeal circuit 6. In the illustrated embodiment the ends comprise the patient end of the arterial line 7 and the patient end of the venous line 8. The patient ends are configured for the connection with the vascular access device for access to the patient vascular system. The patient ends of each line 7 and 8 are opposite the corresponding device ends which are instead configured for connection with the blood chamber 3 of the membrane device 2. The venous line 8 is provided with a pressure sensor 19. Both the arterial line 7 and the venous line 8 are provided with a blocking clamp 20 commanded by the control unit (not illustrated for reasons of simplicity). The apparatus of FIG. 2 can be provided, alternatively or in addition to the sources 9 and 9', with a second further source 9" (represented by a broken line) which comprises a container of priming fluid connected to the arterial line 7, for example via an auxiliary line. The drainage 11 of the apparatus of FIG. 2 can comprise a drainage like the one in FIG. 7 or FIG. 8, in which the same elements of the drainage of FIGS. 5 and 6 have been denoted using the same numbers. With respect to the latter, they exhibit two check valves 21, one for each discharge line 22 connected to the respective arterial line 7 or venous line 8. The functioning of the drainages of FIGS. 7 and 8 is substantially like the functioning of the drainages of FIGS. 5 and 6, with the possible difference that one of the clamps 20 (for example the venous clamp) is closed during the above-described procedure in operation a) of controlling the flow rate (for example in the arterial line when the venous clamp is closed) and in operation b) of acquiring the pressure (for example in the arterial line when the venous clamp is closed).

Figure 3:
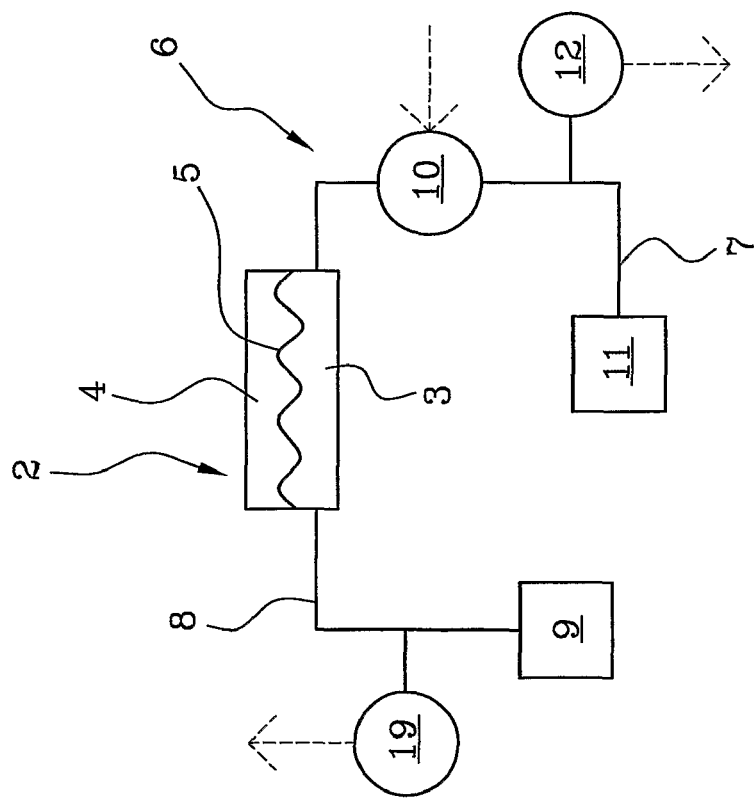
FIG. 3 illustrates a third embodiment of an apparatus for extracorporeal blood treatment in agreement with the present invention.

With reference to FIG. 3, the elements which are the same as in FIGS. 1 and 2 have been denoted using the same numbers. In this case the patient end of the venous line 8 is connected to priming fluid source 9, while the patient end of the arterial line 8 is connected to the drainage 11. Alternatively the patient end of the venous line 8 can be connected to the drainage 11, and the patient end of the arterial line 8 to the priming fluid 9 source. The drainage 11 can comprise one or the other of the configurations of FIGS. 5 and 6.

In reference to FIG. 4, the elements from FIGS. 1 to 3 which are the same have been indicated using the same numbers. In this case the arterial line 7 and the venous line 8 are connected to one another such as to form a ring conformation. A discharge line branches from the ring to connect to the drainage 11. The two patient ends of the arterial line 7 and the venous line 8 can be coupled to one another 8 for example by means of an intermediate connector of known type and not illustrated): in this case the discharge line branching from the ring could be a service line of the arterial line or the venous line, such as for example a line connected to the top of a blood/air separation chamber of the arterial line or the venous line. It is also possible to form the ring configuration by conjoining a patient end (of the arterial line 7 or the venous line 8) to an end of a service line (connected to the venous line 8 or, respectively, to the arterial line 7); in this case the other patient end (of the venous line 8 or, respectively, of the arterial line 7) is connected to the drainage 11. The drainage 11 of the apparatus of FIG. 4 can comprise any of the configurations of FIGS. 5 and 6.

With reference to the apparatus of FIGS. from 2 to 4, the recognition procedures of the type of extracorporeal circuit, performed by the control unit of the various apparatus (similar to unit 13 of FIG. 1 and not illustrated) comprise the above-described recognition procedures.

The recognition systems herein described, of the present invention, enable recognition of whether an extracorporeal circuit of the disposable type for adults has been mounted on the treatment apparatus in the place of one for children, and vice versa. In this way an accidental exchange of circuits, which could cause damage to a patient, can be avoided.

The treatment's prescription set values may include an adult/child patient categorization. Each of the above described apparatus may be configured with an adult/child mode detection. In this case the treatment prescription comprises the adult/child selection. The detection process of the present invention is then activated during the priming procedure. If the detection process recognizes that the blood circuit matches the adult/child selection, no alert to the user is generated, otherwise the controller operates an automatic intervention, e.g. a stop of the priming procedure and/or an alert to the user (alarm/warning visible on the screeen and/or audible). If the apparatus is not configured with an adult/child mode detection, then a treatment detection can be activated during the priming mode; if an adult (or child) line is detected, then a reminder or notice, for example "adult (or child) line detected", is displayed on the screen of the user interface and a request for confirmation is further displayed before connecting the patient or during the priming procedure.

The invention claimed is:

1. An apparatus for extracorporeal blood treatment, comprising:
    a membrane device for extracorporeal blood treatment, comprising a blood chamber and a fluid chamber which are separated from one another by a semipermeable membrane;
    an extracorporeal circuit connected to the blood chamber of the membrane device;
    a source of a priming fluid connected to the extracorporeal circuit;
    a pump connected to the extracorporeal circuit for fluid displacement;
    a drainage connected to an end of the extracorporeal circuit for discharge of the priming fluid;
    a pressure sensor connected to the extracorporeal circuit;
    a memory storing at least a reference value for discriminating at least a first type of extracorporeal circuit from at least a second type of extracorporeal circuit, the first type of extracorporeal circuit being different from the second type of extracorporeal circuit in that there is a difference in a nominal section of fluid passage therethrough;
    a processor connected to the pump, to the pressure sensor and to the memory, the processor being programmed to perform following operations:
    i. controlling the pump to move the priming fluid along the extracorporeal circuit to a first flow rate value;
    ii. receiving from the pressure sensor a first pressure value at the first flow rate value;
    iii. receiving the reference value from the memory;
    iv. processing the first flow rate value and/or the first pressure value with the reference value;
    v. determining, on the basis of the result of the above processing, if the extracorporeal circuit belongs or not to the first type or the second type of extracorporeal circuit.

2. The apparatus of claim 1, wherein said processing operation comprises calculating a parameter indicating a flow resistance of a tract of extracorporeal circuit in nominal conditions, said calculation using a mathematical model which relates the pressure, the flow rate and the resistance to flow rate in the tract of extracorporeal circuit.

3. The apparatus of claim 1, wherein the extracorporeal circuit is configured such that during said operation of controlling the pump for displacing the priming fluid along the extracorporeal circuit at a first flow rate value, the priming fluid is displaced towards the drainage.

4. The apparatus of claim 3, comprising means for maintaining a constant pressure in the drainage while the priming fluid is displaced towards the drainage at a first flow rate value.

5. The apparatus of claim 3, wherein the processor is programmed to perform further operations of:
    vi. acquiring a pressure value at the drainage; and
    vii. using the pressure value at the drainage in said processing operation.

6. The apparatus of claim 1, wherein at least a part of the extracorporeal circuit is configured as a ring so that during said operation of controlling the pump to displace the priming fluid along the extracorporeal circuit at a first flow rate, the priming fluid is recycled along the ring.

7. The apparatus of claim 1, wherein the reference value is indicative of a flow resistance of a reference tract of extracorporeal circuit in nominal conditions.

8. The apparatus of claim 1, wherein the reference value is a reference pressure value, and wherein said processing operation comprises a comparison of the first pressure value with the reference pressure value.

9. The apparatus of claim 1, wherein the reference value is a reference flow rate value, and wherein said processing operation comprises comparing the first flow rate value with the reference flow rate value.

10. The apparatus of claim 1, wherein the at least a reference value comprises a plurality of value ranges, each of the plurality of value ranges being associated to a corresponding type of extracorporeal circuit.

11. The apparatus of claim 1, wherein the processor is programmed to provide, on the basis of the determination of the type of circuit to which the extracoporeal circuit belongs, a setting for performing a treatment.

12. The apparatus of claim 1, wherein the processor is programmed to perform further operations of:
    viii. acquiring a setting for a treatment to be performed with the extracorporeal circuit;
    ix. verifying whether or not the type of circuit to which the extracorporeal circuit belongs is compatible with the treatment to be performed.

13. The apparatus of claim 1, wherein the processor is programmed to perform following operations of:
    x. controlling the pump to displace the priming fluid along the extracorporeal circuit at a second flow rate;
    xi. receiving a second pressure value from the pressure sensor at the second flow rate;
    xii. processing the first and second flow rates and/or the first and second pressure values with the reference value;
    xiii. on the basis of the result of said processing, determining whether the extracorporeal circuit belongs to the first or second type of extracorporeal circuit.

14. The apparatus of claim 1, wherein the pump is a blood pump coupled to the extracorporeal circuit.

15. The apparatus of claim 1, wherein the first pressure value, or the first flow rate value, is a preset value.

16. The apparatus of claim 1, wherein the pressure sensor operates in a tract of the extracorporeal circuit arranged between the pump and the end for the discharge of the priming fluid.

17. A method for readying an extracorporeal blood treatment apparatus, comprising stages of:
    providing a membrane device for extracorporeal blood treatment, comprising a blood chamber and a fluid chamber separated by a semipermeable membrane;
    connecting an extracorporeal circuit to the blood chamber of the membrane device;
    connecting a priming fluid source to the extracorporeal circuit;
    connecting a fluid displacement pump to the extracorporeal circuit;
    connecting a drainage for priming fluid discharge to an end of the extracorporeal circuit;
    connecting a pressure sensor to the extracorporeal circuit;
    storing in a memory at least a reference value for discriminating at least a first type of extracorporeal circuit from at least a second type of extracorporeal circuit, the first type of extracorporeal circuit being different from the second type of extracorporeal circuit by a nominal section of fluid passage;
    controlling the pump to displace the priming fluid along the extracorporeal circuit to a first flow rate value;

taking a first pressure value reading from the pressure sensor at the first flow rate;

processing the first flow rate and/or the first pressure value with the reference value;

determining, on the basis of the result of said processing, whether or not the extracorporeal circuit belongs to the first type or the second type of extracorporeal circuit.

18. The method of claim 17, wherein the stage of processing comprises calculating a parameter which is indicative of a flow resistance of a tract of extracorporeal circuit in nominal conditions, the calculation using a mathematical model which relates the pressure, the flow rate and the flow resistance of the tract of circuit.

19. The method of claim 17, comprising a stage of configuring the extracorporeal circuit such that, during the stage of controlling the pump to displace the priming fluid along the extracorporeal circuit at a first flow rate, the priming fluid is displaced towards the drainage.

20. The method of claim 19, comprising a stage of maintaining a constant pressure in the drainage while the priming fluid is displaced towards the drainage at a first flow rate.

21. The method of claim 19, comprising further stages of:
acquiring a pressure value at the drainage; and
using the pressure value at the drainage in said processing stage.

22. The method of claim 17, comprising a stage of configuring at least a part of the extracorporeal circuit in a ring and recycling the priming fluid along the ring during the stage of controlling the pump to displace the priming fluid along the extracorporeal circuit at a first flow rate.

23. The method of claim 17, wherein the reference value is indicative of a flow resistance of a reference tract of extracorporeal circuit in nominal conditions.

24. The method of claim 17, wherein the reference value is a reference pressure value, and wherein the stage of processing comprises comparing the first pressure value with the reference pressure value.

25. The method of claim 17, wherein the reference value is a reference flow rate value, and wherein the stage of processing comprises comparing the first flow rate value with the reference flow rate value.

26. The method of claim 17, wherein the at least a reference value comprises a plurality of value ranges, each range being associated to a corresponding type of extracorporeal circuit.

27. The method of claim 17, comprising a further stage of providing, on the basis of the determination of the type of circuit to which the extracorporeal circuit belongs, a setting for performing a treatment.

28. The method of claim 17, comprising further stages of:
acquiring a setting of a treatment to be performed with the extracorporeal circuit;
verifying whether or not the type of circuit to which the extracorporeal circuit belongs is compatible with the treatment to be performed.

29. The method of claim 17, comprising further stages of:
controlling the pump for displacing the priming fluid along the extracorporeal circuit at a second flow rate value;
receiving a second pressure value from the pressure sensor at the second flow rate value;
processing the first and the second flow rate values and/or the first and the second pressure values with the reference value;
determining, based on the result of said processing, whether or not the extracorporeal circuit belongs to the first type or the second type of extracorporeal circuit.

30. The method of claim 17, wherein the pump is a blood pump which is coupled to the extracorporeal circuit.

31. The method of claim 17, comprising a stage of presetting the first pressure value, or the first flow rate value.

32. The method of claim 17, comprising a stage of predisposing the pressure sensor for operating in a tract of the extracorporeal circuit arranged between the pump and the end for the priming fluid discharge.

* * * * *

UNITED STATES PATENT AND TRADEMARK OFFICE
CERTIFICATE OF CORRECTION

PATENT NO.        : 8,388,567 B2
APPLICATION NO.   : 12/595164
DATED             : March 5, 2013
INVENTOR(S)       : Paolo Rovatti It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 798 days.

Signed and Sealed this
First Day of September, 2015

Michelle K. Lee
*Director of the United States Patent and Trademark Office*